United States Patent
Kimura et al.

(10) Patent No.: US 7,591,954 B2
(45) Date of Patent: Sep. 22, 2009

(54) METHOD FOR REMOVING LEUKOCYTES, LEUKOCYTE-REMOVING FILTER AND UTILIZATION THEREOF

(75) Inventors: Masayuki Kimura, Oita (JP); Yukihiro Yamada, Oita (JP)

(73) Assignee: Asahi Kasei Medical Co., Ltd., Tokyo (JP)

( * ) Notice: Subject to any disclaimer, the term of this patent is extended or adjusted under 35 U.S.C. 154(b) by 347 days.

(21) Appl. No.: 10/537,252

(22) PCT Filed: Dec. 2, 2003

(86) PCT No.: PCT/JP03/15398

§ 371 (c)(1),
(2), (4) Date: Feb. 7, 2006

(87) PCT Pub. No.: WO2004/050146

PCT Pub. Date: Jun. 17, 2004

(65) Prior Publication Data

US 2006/0184085 A1 Aug. 17, 2006

(30) Foreign Application Priority Data

Dec. 2, 2002 (JP) .............................. 2002-349329

(51) Int. Cl.
B01D 37/00 (2006.01)
B01D 29/00 (2006.01)
B01D 39/00 (2006.01)

(52) U.S. Cl. ................. 210/767; 210/488; 210/490; 210/491; 210/503; 210/504; 210/505; 210/506; 264/172.11; 264/172.17

(58) Field of Classification Search ............... None
See application file for complete search history.

(56) References Cited

U.S. PATENT DOCUMENTS

| | | | |
|---|---|---|---|
| 4,701,267 A | 10/1987 | Watanabe et al. | |
| 5,476,587 A | 12/1995 | Kuroki et al. | |
| 5,478,470 A | 12/1995 | Fukuda et al. | |
| 5,543,062 A * | 8/1996 | Nishimura | 210/782 |
| 5,665,233 A | 9/1997 | Fukuda et al. | |
| 5,707,520 A | 1/1998 | Kuroki et al. | |
| 5,817,237 A * | 10/1998 | Lee et al. | 210/645 |
| 5,935,436 A * | 8/1999 | Lee et al. | 210/257.1 |
| 6,048,464 A | 4/2000 | Tanaka et al. | |
| 2002/0121194 A1 | 9/2002 | Buchwald et al. | |

FOREIGN PATENT DOCUMENTS

| | | |
|---|---|---|
| EP | 0 155 003 | 9/1985 |
| EP | 0 811 412 | 12/1997 |
| EP | 1208900 | 5/2002 |
| JP | 63-175156 | 1/1988 |
| JP | 63-175157 | 7/1988 |
| JP | 1-224324 | 9/1989 |
| JP | 2-013587 | 4/1990 |
| JP | 7-124255 | 5/1995 |
| JP | 9-155127 | 6/1997 |
| JP | 2811707 | 8/1998 |
| JP | 11-094767 | 4/1999 |
| JP | 2002-220773 | 8/2002 |
| WO | 96/03194 | 2/1996 |
| WO | 93/03740 | 3/1999 |
| WO | 2006-073106 | 12/2005 |

OTHER PUBLICATIONS

U.S. Appl. No. 11/813,329 to Kenji Kobayashi, filed Dec. 28, 2005 which is the national stage of PCT/JP2005/024035.
English Language Abstract of JP 1-224324.
English Language Abstract of JP 9-155127.
English Language Abstract of JP 7-124255.
English Language Abstract of JP 2811707.
English Language Abstract of JP 11-094767.
U.S. Appl. No. 11/569,901, filed Dec. 6, 2006 371 filed Jun. 9, 2005.
U.S. Appl. No. 11/675,275, filed Feb. 15, 2007.
U.S. Appl. No. 11/813,329, filed Oct. 5, 2007 371 filed Dec. 28, 2005.
U.S. Appl. No. 10/575,099, filed Feb. 6, 2007 371 filed Oct. 8, 2004.
English Language Abstract of JP 1-224324, Dec. 26, 2005.
English Language Abstract of JP 9-155127, Dec. 26, 2005.
English Language Abstract of JP 7-124255, Dec. 26, 2005.
English Language Abstract of JP 2811707, Jan. 7, 2005.
English Language Abstract of JP 11-094767, Jan. 7, 2005.

* cited by examiner

Primary Examiner—Cecilia Tsang
Assistant Examiner—Julie Ha
(74) Attorney, Agent, or Firm—Greenblum & Bernstein, P.L.C.

(57) ABSTRACT

A method for removing leukocytes, whereby leukocytes can be removed at a higher level of performance in a short filtration time without clogging. A method comprising passing a leukocyte-containing liquid through a filter for removing leukocytes made of a nonwoven fabric having an average fiber diameter of from 0.3 to 3.0 μm, and thus removing the leukocytes from the leukocyte-containing liquid, to give a leukocyte-free liquid, characterized by using a nonwoven fabric having a formation index (y) of 50 or less corresponding to a thickness of 0.3 mm; use of a leukocyte removal filter therefore; and the leukocyte removal filter.

10 Claims, 3 Drawing Sheets

METHOD FOR REMOVING LEUKOCYTES, LEUKOCYTE-REMOVING FILTER AND UTILIZATION THEREOF

TECHNICAL FIELD

The present invention relates to a method for removing leukocytes from a leukocyte-containing liquid such as a blood product for blood transfusion, such as a whole blood product, red cell product, platelet product, or plasma product, or an intermediate for preparing the blood product, by using a specific leukocyte removal filter to obtain a leukocyte-free liquid. The present invention also relates to a method for removing leukocytes in extracorporeal circulation by using a specific leukocyte removal filter to obtain a leukocyte-free liquid.

BACKGROUND ART

In the field of blood transfusion, blood component transfusion comprising separating a blood component necessary for a recipient from a whole blood product and transfusing the blood component into the recipient has been commonly practiced in addition to whole blood transfusion comprising transfusing a whole blood product, obtained by adding an anticoagulant to blood collected from a donor, into a recipient The blood component transfusion is classified into red cell transfusion, platelet transfusion, plasma transfusion, and the like depending on the type of the blood component necessary for a recipient. The blood product used for the blood component transfusion includes a red cell product, platelet product, plasma product, and the like.

In recent years, leukocyte-free blood transfusion in which a blood product is transfused after removing leukocytes contained in the blood product has been widely used. This is because it was found that relatively slight side effects accompanying blood transfusion, such as headache, nausea, chill, or febrile nonhemolytic reaction, or serious side effects which seriously affect a recipient, such as alloantigen sensitization, viral infection, or posttransfusion graft versus host disease (GVHD), are mainly caused by leukocytes contained in the blood product used for blood transfusion.

It is considered that relatively slight side effects such as headache, nausea, chill, or fever can be prevented by removing leukocytes in the blood product until the leukocyte residual rate becomes 10-1 to 10-2 or less. It is considered that leukocytes must be removed until the residual rate becomes 10-4 to 10-6 or less in order to prevent serious side effects such as alloantigen sensitization or viral infection.

In recent years, leukocyte removal therapy using extracorporeal blood circulation has been conducted for treating diseases such as rheumatism or ulcerative colitis, and has achieved excellent clinical effects.

Methods of removing leukocytes from the blood product are roughly classified into two kinds of methods of a centrifugation method in which leukocytes are separated and removed using a centrifuge by utilizing the difference in specific gravity among blood components, and a filter method in which leukocytes are removed by using a filter material comprising fiber mass such as nonwoven fabric, a porous structure having continuous pores or the like. The filter method which removes leukocytes by means of adhesion or adsorption is most widely used at present because this method has advantages such as simplified operation and low cost.

In the leukocyte removal mechanism using the filter material such as fiber mass such as nonwoven fabric or a porous structure having continuous pores, it is considered that leukocytes coming into contact with the surface of the filter material adhere to or are adsorbed on the surface of the filter material. Therefore, as means for improving the leukocyte removal performance of the conventional filter material, a method of increasing the contact frequency between the filter material and leukocytes, specifically, studies of reducing the fiber diameter or the pore size of the nonwoven fabric or increasing the bulk density have been proceeded (Japanese Patent No. 1723513 (JP-1723513)). However, since the pressure drop is increased when causing the blood product to pass through the filter material accompanying improvement of the leukocyte removal performance, there has been a problem that the filtration speed is significantly decreased before completing the filtration of a desired amount of blood.

On the other hand, as to the porous structure having continuous pores, a porous product having a bubble point of 0.08 to 0.3 kg/cm$^2$ is disclosed as a leukocyte separation material free from clogging with leukocytes (Japanese Patent Application Laid-Open No. 01-224324 (JP-A-01-224324)). However, the inventors of the present invention examined and found that this leukocyte separation material is suitable for reducing leukocytes contained in the blood product to $10^{-2}$ to $10^{-3}$, but poses the following problem when using a porous product having a relatively small average pore size necessary for achieving a leukocyte residual rate of $10^{-4}$ which is the target value of the present invention. Specifically, a porous product with an optimal pore size exhibits a leukocyte removal performance equal to that of nonwoven fabric at a thickness several times smaller than that of the nonwoven fabric, and may provide promising means in achieving a reduction in size. However, a porous product exhibiting such a high leukocyte removal performance shows a large degree of pressure drop due to clogging with leukocytes, whereby the blood filtration speed is significantly decreased in the same manner as in the case of using nonwoven fabric having a small fiber diameter.

In recent years, the medical treatment field has posed additional demands for the leukocyte removal filter. One of the demands is improvement of the recovery rate of useful components in addition to improvement of the leukocyte removal performance. At present, useful components remaining in the filter and the circuit are collected by using a physiological saline solution or air in order to increase the recovery rate of useful components. However, it is important to save labor by making such an operation unnecessary. Blood as the raw material for the blood product is mainly valuable blood provided by a goodwill blood donation. However, uncollectible blood remaining in the leukocyte removal filter is disposed of together with the filter and frittered away. Therefore, it is extremely meaningful to improve the recovery rate of useful components in comparison with the existing leukocyte removal filter.

Therefore, in order to satisfy the above-described demand in the medical treatment field, a leukocyte removal filter device using a leukocyte removal filter material having a high leukocyte removal performance per unit volume and packed with a smaller amount of filter material than ever before has been demanded. Use of such a device reduces the amount of blood remaining in the filter due to a reduction in the amount of filter material packed and makes it unnecessary to perform the operation of collecting useful components remaining in the filter, whereby the recovery rate of useful components is expected to be increased in comparison with a conventional filter device.

As another demand for the leukocyte removal filter in the market, there is a demand for treating a desired amount of blood in a short period of time. In order to satisfy such a demand, the leukocyte removal filter device is considered to have such a shape that the cross-sectional area of the device is equal to or greater than that of a conventional device and the thickness of the filter material is reduced. However, it is necessary to increase the leukocyte removal performance per unit volume in order to reduce the thickness of the filter material while maintaining the leukocyte removal performance.

In order to satisfy such demands, attempts to improve the leukocyte removal performance per unit volume have been made by improving uniformity of the property elements of the filter material. As a general filter material in which the property elements are made uniform, a nonwoven fabric filter material in which the pore size of the nonwoven fabric used as the filter material is made uniform and the pore size distribution in which fibers having different thicknesses exist is made narrow, nonwoven fabric of which the fiber diameter is uniform, which does not include overlapping fibers, and of which weight per square meter (metsuke) is made uniform, and the like can be given (JP-A-63-175156, JP-A-09-155127, and WO 96/03194).

In the technical field aiming at removing leukocytes, as a material in which the property elements of the filter material are made uniform, a leukocyte trapping material in which the volume of the pore section useful for leukocyte removal is increased by narrowing the pore size distribution, and a three-dimensional mesh-like continuous porous product having a uniform pore size in which the ratio of the volume average pore size to the number average pore size is 1.5 to 2.5 have been proposed. As nonwoven fabric as the filter material, nonwoven fabric in which uniformity of the fiber diameter is improved by narrowing the fiber diameter distribution has been proposed (WO 93/03740, JP-A-07-124255, JP-A-63-175157, and JP-2811707).

As described above, attempts to increase the leukocyte removal performance per unit volume have been proceeded by making the pore size or the fiber diameter of the filter material uniform. However, the leukocyte removal performance of the leukocyte removal filter or flowability during filtration is not necessarily improved by making the pore size or the fiber diameter of the filter material uniform. Specifically, since blood flows through the filter material in the thickness direction, if the property elements of the filter material in the thickness direction are nonuniform in the filtration surface direction, blood tends to flow through the portion of the filter material in which the liquid-flow resistance is low, even if the pore size or the fiber diameter is uniform. As a result, since filtration is completed without the entire filter material being uniformly utilized, a sufficient leukocyte removal performance cannot be obtained. Moreover, since clogging tends to occur in the portion in which a large amount of blood flows due to a decrease in the substantial liquid-flow area, the filtration time is increased. Therefore, the leukocyte removal performance per unit volume is improved in a microscopic sense by making the pore size or the fiber diameter uniform. However, in a macroscopic sense, if the pores in the nonwoven fabric as the filter material are not uniformly arranged, or the fiber is unevenly distributed, or the weight per square meter of the filter material is nonuniform, since blood tends to flow through the portion having a low liquid-flow resistance, a sufficient filter performance cannot be achieved. As described above, the conventional technologies merely intend to make a single property element represented by the fiber diameter and the average pore size uniform, but do not recognize the importance of uniformity over the entire filter material.

DISCLOSURE OF THE INVENTION

In order to solve the above-described problems in the conventional technologies and to satisfy the additional demands from the medical treatment field, an objective of the present invention is to provide a leukocyte removal method exhibiting a higher leukocyte removal performance and reducing the filtration time without causing clogging by using a specific leukocyte removal filter.

The inventors of the present invention conducted extensive studies on the case of treating a leukocyte-containing liquid, which tends to cause clogging due to high viscosity, using a leukocyte removal filter, while paying attention to the importance of uniformity of nonwoven fabric as the filter material. As a result, the inventors have found that a leukocyte removal method exhibiting a high leukocyte removal performance and reducing the filtration time without causing clogging can be obtained by using a leukocyte removal filter in which a specific structure in the thickness direction, that is, the liquid flow direction, is made uniform over the entire filtration surface of the nonwoven fabric instead of making only a single property element uniform as known in the art.

Specifically, the present invention includes followings.

1. A method for removing leukocytes comprising causing a leukocyte-containing liquid to pass through a leukocyte removal filter comprising nonwoven fabric having an average fiber diameter of 0.3 to 3.0 μm to remove leukocytes from the leukocyte-containing liquid and to obtain a leukocyte-free liquid, and further comprising using nonwoven fabric having a formation index y of 50 or less corresponding to a thickness of 0.3 mm.

2. The method for removing leukocytes wherein the nonwoven fabric has a filling rate of 0.05 to 0.30.

3. The method for removing leukocytes wherein the nonwoven fabric has a formation index y of 50 or less corresponding to a thickness of 0.3 mm, and y satisfied the following inequality.

$$y < -4 \times \text{average fiber diameter of nonwoven fabric } (\mu m) + 55$$

4. The method for removing leukocytes wherein the nonwoven fabric is obtained by using a melt-blown method.

5. The method for removing leukocytes comprising: using a leukocyte removal filter comprising a filter for removing aggregate upstream of the nonwoven fabric and/or a post-filter downstream of the nonwoven fabric.

6. The method for removing leukocytes wherein the leukocyte removal filter is a flat filter having an inlet and an outlet for liquid.

7. The method for removing leukocytes wherein the leukocyte removal filter is a cylindrical filter having an inlet and an outlet for liquid.

8. The method for removing leukocytes wherein a container of the leukocyte removal filter is formed of a flexible resin.

9. The method for removing leukocytes comprising: causing the leukocyte-containing liquid selected from whole blood, red cell concentrate, platelet concentrate, platelet rich plasma, and platelet poor plasma to pass through the leukocyte removal filter.

10. The method for removing leukocytes comprising: causing the leukocyte-containing liquid to pass through the leukocyte removal filter by utilizing head drop.

11. The method for removing leukocytes comprising: causing the leukocyte-containing liquid to pass through the leukocyte removal filter by increasing pressure of the inlet side of the leukocyte removal filter and/or reducing pressure of the outlet side of the leukocyte removal filter.

12. The method for removing leukocytes comprising: performing extracorporeal circulation by continuously collecting whole blood from a body of a patient, causing the collected whole blood to pass through the leukocyte removal filter, and returning the leukocyte-free whole blood to the body of the patient.

13. Use of a leukocyte removal filter having a formation index y of 50 or less corresponding to a thickness of 0.3 mm for a leukocyte removal method comprising removing leukocytes from a leukocyte-containing liquid by using a leukocyte removal filter comprising nonwoven fabric having an average fiber diameter of 0.3 to 3.0 to μm.

14. The use of a leukocyte removal filter wherein the nonwoven fabric has a filling rate of 0.05 to 0.30.

15. The use of a leukocyte removal filter wherein the nonwoven fabric has a formation index y of 50 or less corresponding to a thickness of 0.3 mm, and y satisfied the following inequality.

$$y < -4 \times \text{average fiber diameter of nonwoven fabric (μm)} + 55$$

16. The use of a leukocyte removal filter wherein the nonwoven fabric is obtained by using a melt-blown method is used.

17. The use of a leukocyte removal filter wherein the leukocyte removal filter comprises a filter for removing aggregate upstream of the nonwoven fabric and/or a post-filter downstream of the nonwoven fabric.

18. The use of a leukocyte removal filter wherein the leukocyte removal filter is a flat filter having an inlet and an outlet for liquid.

19. The use of a leukocyte removal filter wherein the leukocyte removal filter is a cylindrical filter having an inlet and an outlet for liquid.

20. The use of a leukocyte removal filter wherein a container of the leukocyte removal filter is formed of a flexible resin.

21. The use of a leukocyte removal filter for removing leukocytes from the leukocyte-containing liquid selected from whole blood, red cell concentrate, platelet concentrate, platelet rich plasma, and platelet poor plasma.

22. The use of a leukocyte removal filter for causing the leukocyte-containing liquid to pass through the leukocyte removal filter by utilizing head drop.

23. The use of a leukocyte removal filter for causing the leukocyte-containing liquid to pass through the leukocyte removal filter by increasing pressure of the inlet side of the leukocyte removal filter and/or reducing pressure of the outlet side of the leukocyte removal filter.

24. The use of a leukocyte removal filter for continuously collecting whole blood from a body of a patient and causing the collected whole blood to pass through the leukocyte removal filter.

25. A leukocyte removal filter for a leukocyte removal method for removing leukocytes from a leukocyte-containing liquid, comprising: nonwoven fabric having an average fiber diameter of 0.3 to 3.0 μm and a formation index y of 50 or less corresponding to a thickness of 0.3 mm.

26. The leukocyte removal filter wherein the nonwoven fabric has a filling rate of 0.05 to 0.30.

27. The leukocyte removal filter wherein the nonwoven fabric has a formation index y of 50 or less corresponding to a thickness of 0.3 mm, and y satisfies the following inequality.

$$y < -4 \times \text{average fiber diameter of nonwoven fabric (μm)} + 55$$

28. The leukocyte removal filter, wherein the nonwoven fabric is obtained by using a melt-blown method.

29. A leukocyte removal filter, comprising: a filter for removing aggregate upstream of the nonwoven fabric and/or a post-filter downstream of the nonwoven fabric.

30. The leukocyte removal filter, comprising a flat filter having an inlet and an outlet for liquid.

31. The leukocyte removal filter, comprising a cylindrical filter having an inlet and an outlet for liquid.

32. The leukocyte removal filter wherein a container of the filter is formed of a flexible resin.

33. The leukocyte removal filter, wherein the leukocyte removal filter is used to remove leukocytes from the leukocyte-containing liquid selected from whole blood, red cell concentrate, platelet concentrate, platelet rich plasma, and platelet poor plasma.

34. A blood extracorporeal circulation device for blood, comprising: at least the leukocyte removal filter.

35. A blood extracorporeal circulation device for blood, comprising: at least the leukocyte removal filter an inlet for introducing whole blood collected from a body of a patient into the leukocyte removal filter; and an outlet for returning the leukocyte-free whole blood to the body of the patient.

BEST MODE FOR CARRYING OUT THE INVENTION

The present invention is described below in detail.
The leukocyte-containing liquid used in the present invention refers to the generic name for a body fluid and synthetic blood containing leukocytes. In more detail, the leukocyte-containing liquid refers to whole blood and a single or multiple blood component-containing liquid prepared from whole blood, such as whole blood, red cell concentrate, washed red cell suspension, frozen thawed concentrated red cells, synthetic blood, platelet poor plasma (PPP), platelet rich plasma (PRP), plasma, frozen plasma, platelet concentrate, and buffy coat (BC), a solution in which an anticoagulant, a preservative solution, or the like is added to the above-mentioned liquid, or a whole blood product, a red cell product, a platelet product, a plasma product, and the like. A liquid obtained by treating the above-mentioned liquid using the method of the present invention is called a leukocyte-free liquid.

In the present invention, a leukocyte-free liquid may be obtained by causing the above-mentioned leukocyte-containing liquid to pass through a leukocyte removal filter comprising specific nonwoven fabric, that is, highly uniform nonwoven fabric in which a specific structure in the flow direction is made uniform over the entire filtration surface. The term "highly uniform nonwoven fabric" used herein refers to nonwoven fabric of which the formation index, which is an index for evaluating the degree to which the structure in the thickness direction varies in the direction of the surface perpendicular to the thickness direction, is within a specific range.

The formation index used in the present invention is a value obtained by irradiating light from the bottom of the nonwoven fabric, detecting the transmitted light using a charge-coupled device camera (hereinafter abbreviated as "CCD camera"), and multiplying the coefficient of variation (%) of the absorbance of the porous product detected by each pixel of the CCD camera by ten.

The specific calculation method is as follows.

(1) The transmittance for each pixel is determined using a CCD camera.

Transmittance=(light intensity during light-on–light intensity during light-off)/(light intensity during light-on without sample–light intensity during light-off without sample)×100(%)

(2) The transmittance for each pixel is converted into absorbance using the following equation.

Absorbance=2−log(transmittance)

(3) The mean value and the standard deviation of the absorbance are calculated.

(4) The coefficient of variation is calculated using the following equation.

Coefficient of variation=standard deviation of absorbance/mean absorbance×100(%)

(5) The coefficient of variation is multiplied by ten and defined as the formation index.

Formation index=coefficient of variation×10

Figure 4:
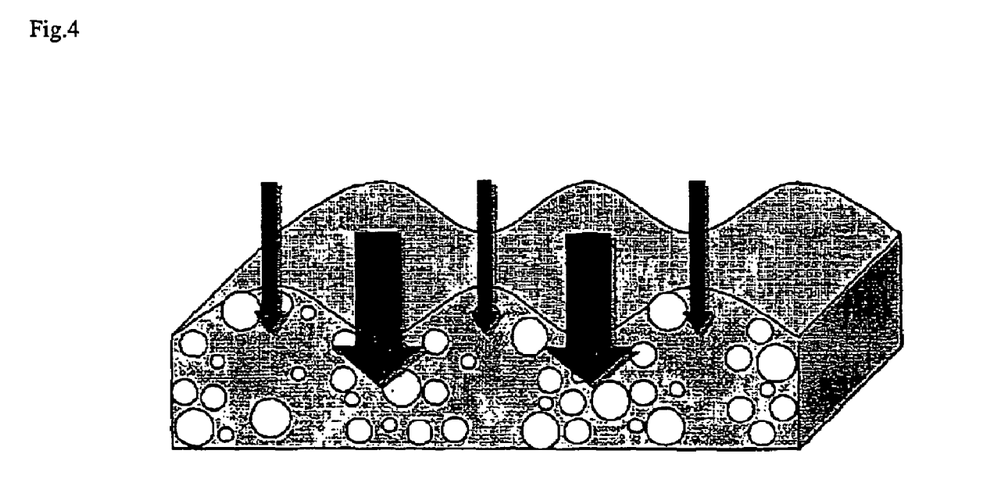
FIG. 4 is a schematic diagram showing the concept of uniformity in a conventional leukocyte removal filter. The direction of the arrow indicates the liquid flow direction, and the width of the arrow indicates flowability. The greater the width, the easier the liquid flows.

The formation index calculation equations (1) to (5) indicate that, as the formation index is increased, the light transmission of the nonwoven fabric becomes nonuniformity, and the property elements of the nonwoven fabric in the thickness direction becomes nonuniformity over the entire area in the filtration surface direction (direction of the surface perpendicular to the thickness direction). The property elements used herein refers to the average fiber diameter, the average pore size (gap formed by fiber dispersion), the weight per square meter, and the like. If the formation index is high, voids in the nonwoven fabric are not uniformly arranged, fiber dispersion is unevenly distributed, or the weight per square meter of the filter material is uneven. In this case, an area having a high liquid-flow resistance and an area having a low liquid-flow resistance occur in the nonwoven fabric. Therefore, when the leukocyte-containing liquid (hereinafter may be simply called "blood or the like") is caused to flow through the nonwoven fabric, the leukocyte-containing liquid is gathered in the area having a low liquid-flow resistance. As a result, since the filter material is not sufficiently utilized in the portion in which the blood or the like flows to only a small extent due to high liquid-flow resistance, the leukocyte removal performance per unit volume is decreased over the entire filter. Moreover, since a decrease in the substantial liquid-flow area or clogging tends to occur due to the concentration of the flow of the blood or the like, the filtration speed is decreased. FIG. 4 schematically shows such a state. As shown in FIG. 4, since the structure in the thickness direction of a certain portion differs from that of another portion, uniformity is not maintained over the entire filtration surface.

Figure 5:
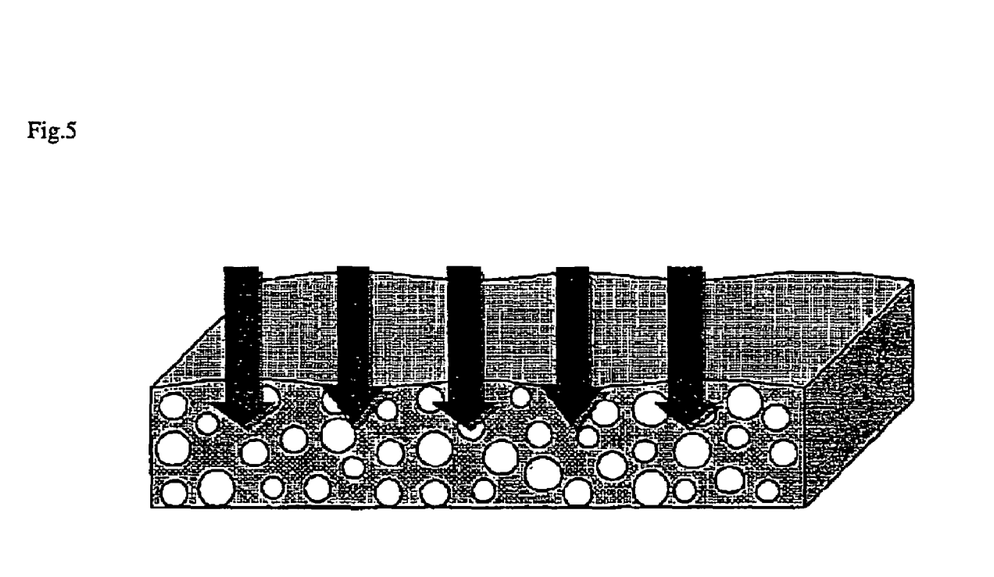
FIG. 5 is a schematic diagram showing the concept of uniformity in the leukocyte removal filter of the present invention.

Contrary, a low formation index indicates that light is uniformly transmitted through the nonwoven fabric. In this case, the structure of the nonwoven fabric in the thickness direction is considered to be uniform over the entire filtration surface. Specifically, a low formation index indicates that the void arrangement in the nonwoven fabric, the fiber dispersion, the weight per square meter of the filter material, and the like are generally uniform. However, this does not necessarily limit uniformity of the individual property element In this case, since the non-uniformity of the liquid-flow resistance does not occur in the nonwoven fabric, a uniform flow can be achieved when causing a liquid such as blood to flow through the nonwoven fabric. As a result, since the filter material is uniformly and sufficiently utilized, the leukocyte removal performance per unit volume is increased over the entire filter. Moreover, since the flow of the blood or the like is widely spread, a decrease in the substantial liquid-flow area or clogging does not occur, whereby the filtration time can be reduced. FIG. 5 schematically shows such a state.

In the present invention, the formation index was measured using a formation tester FMT-MIII (Nomura Shoji Co., Ltd.; manufactured in 2002; S/N: 130). The basic setting of the tester was not changed after the shipment from the factory, and the measurement was carried out at about 3400 of the total number of pixels using a CCD camera. In the present invention, the formation index was measured while adjusting the measurement size to 7×3 cm (one pixel size=0.78×0.78 mm) so that the total number of pixels was about 3400. However, the measurement size may be changed corresponding to the shape of the sample so that the total number of pixels is equal. Since the formation index is significantly affected by the thickness of the nonwoven fabric, the formation index corresponding to a thickness of 0.3 mm was calculated using the following method. Specifically, three sheets of nonwoven fabric having substantially same quality and a uniform thickness of 0.3 mm or less are provided, and the formation index and the thickness of each sheet are measured. The thickness is measured at four points using a thickness meter (Ozaki Mfg. Co., Ltd., Peacock Model G), and the average value is defined as the thickness of the nonwoven fabric. Then, two of the three sheets of nonwoven fabric are placed one upon another so that the thickness is 0.3 mm or more, and the formation index and the thickness are measured. After completing the formation index measurement for all three combinations, a linear regression equation of the thickness and the formation index is created, and the formation index at a thickness of 0.3 mm is calculated using the equation. In the case where the total thickness of the two sheets of nonwoven fabric does not reach 0.3 mm, sheets of nonwoven fabric are placed one upon another so that the thickness is 0.3 mm, and the formation index is measured. The number of sheets of nonwoven fabric is then reduced so that the thickness is 0.3 mm or less, and the formation index is measured. The formation indices are measured for all nonwoven fabric combinations in which the total thickness is 0.3 mm or less. Then, a linear regression equation of the thickness and the formation index is created, and the formation index at a thickness of 0.3 mm is calculated using the equation. The nonwoven fabric having substantially same quality means that the properties of the nonwoven fabric (material, fiber diameter, filling rate, and the like) are identical. In the case where sheets of nonwoven fabric having substantially same quality necessary for measurement cannot be obtained from a single filter, the formation index may be measured by combining sheets of nonwoven fabric of the same type of filter.

In the leukocyte removal method of the present invention, it is necessary to use a leukocyte removal filter comprising nonwoven fabric having a formation index y of 50 or less corresponding to a thickness of 0.3 mm. If the formation index y is greater than 50, since the structure of the nonwoven fabric in the thickness direction is nonuniform in the filtration surface direction, blood does not uniformly flow through the nonwoven fabric, whereby a sufficient leukocyte removal performance cannot be obtained. Moreover, a decrease in the substantial liquid-flow area or clogging tends to occur, whereby the filtration speed is decreased.

On the other hand, since it is difficult to manufacture nonwoven fabric having a formation index of less than 15, the requirement for the manufacturing efficiency cannot be satisfied. Therefore, the formation index y is preferably 15 to 50. The formation index y is more preferably 16 to 48, still more preferably 17 to 45, and particularly preferably 17 to 41.

The inventors of the present invention measured the formation index y of a conventional leukocyte removal filter material. As a result, a material having a formation index y of 50 or less was not found.

In order to further improve the leukocyte removal performance per unit volume, it is preferable to use a filter comprising nonwoven fabric having a small fiber diameter and a low formation index. In order to remove leukocytes by using a leukocyte removal filter having a high leukocyte removal performance per unit volume and showing a small degree of blood loss, it is preferable that the formation index y corresponding to a thickness of 0.3 mm of the nonwoven fabric be 50 or less and be lower than the value obtained using the following equation (2).

$$a + \text{average fiber diameter of nonwoven fabric (μm)} + 55, a=-4 \quad (2)$$

If the formation index of the nonwoven fabric is lower than the value y, since the formation index and the average fiber diameter are well-balanced, a high leukocyte removal performance can preferably be obtained without causing clogging. In the equation (2), "a" is still more preferably −4.5, and particularly preferably −5.

The leukocyte removal filter used for the leukocyte removal method of the present invention comprises nonwoven fabric having the above-mentioned formation index. Such highly uniform nonwoven fabric may be manufactured by using either a wet method or a dry method. In particular, the nonwoven fabric is preferably manufactured by using a melt-blown method, a flash spinning method, or a calendering method, since an ultrafine fiber can be obtained.

An example of the melt-blown method is described below as the manufacturing method for the nonwoven fabric in the present invention.

A molten polymer fluid melted in an extruder is filtered through an appropriate filter, introduced into a molten polymer inlet section of a melt-blown die, and discharged from an orifice nozzle. At the same time, a heated gas introduced into a heated gas inlet section is introduced into a heated gas discharging slit formed by the melt-blown die and a lip. The molten polymer discharged is attenuated by discharging the heated gas from the slit to cause ultrafine fibers to be formed and stacked to obtain nonwoven fabric. As the spinning factors which should be examined in order to increase uniformity of the nonwoven fabric structure and to adjust the formation index within the desired range, the resin viscosity, melting temperature, discharging amount per single pore, heated gas temperature, heated gas pressure, distance between the spinning nozzle and the accumulation net, and the like can be given. Nonwoven fabric which satisfies the formation index of the present invention can be obtained by optimizing these spinning factors, specifically, by reducing the resin viscosity while maintaining such a melting temperature that deterioration or thermal decomposition of the resin does not occur, setting the heated gas temperature in such a range that an appropriate cooling effect is obtained for the discharged polymer stream, and setting the distance between the spinning nozzle and the accumulation net to such an extent that fibers are not densified and bundled.

As the material for the nonwoven fabric of the present invention, a polyurethane, poly(meth)acrylate, polyacrylonitrile, polyvinyl acetal, polyester, polyamide, polysulfone, polystyrene, polyethylene, polypropylene, cellulose, cellulose acetate, glass, and the like are suitable. Of these, a polyester, polyamide, polyacrylonitrile, polypropylene, and the like are preferable, with polyethylene terephthalate, polybutylene terephthalate, and polypropylene being particularly preferable.

The average fiber diameter of the nonwoven fabric of the present invention is 0.3 to 3.0 μm, preferably 0.3 to 2.5 μm, and still more preferably 0.5 to 2.0 μm. If the average fiber diameter is greater than 3.0 μm, occurrence of contact with leukocytes is reduced due to a decrease in the specific surface area, whereby it trends to become difficult to trap leukocytes. If the average fiber diameter is less than 0.3 μm, occurrence of clogging caused by blood cells tends to be increased.

The average fiber diameter used in the present invention refers to a value determined according to the following procedure. Specifically, portions of the filter material considered to be substantially uniform are sampled at several points from one sheet of nonwoven fabric making up the filter material or a plurality of sheets of nonwoven fabric having substantially same quality, and photographed using a scanning electron microscope or the like. The filter material is continuously photographed until the total number of fibers photographed exceeds 100, and the diameters of all the fibers appearing in the photographs thereby obtained are measured. The diameter used herein refers to the width of the fiber in the direction perpendicular to the fiber axis. A value obtained by dividing the sum of the diameters of all the fibers measured by the number of fibers is defined as the average fiber diameter. However, when plural fibers are overlapped each other, and a fiber is hidden behind another fiber, whereby the width cannot be measured, when fibers are melted to form a thick fiber, when fibers with diameter significantly differing from each other are mixed, when the boundary of the fibers is not clear due to incorrect focusing, or the like, the data obtained is eliminated. If the average fiber diameter significantly differs between the upstream side and the downstream side, such a material is not considered to be a single filter material. The term "the average fiber diameter significantly differs" used herein refers to the case where a significant difference is statistically recognized. In this case, the upstream side and the downstream side of the material are considered to be different filter materials, and the average fiber diameters of the upstream side and the downstream side are separately measured after identifying the interface between the upstream side and the downstream side.

The filling rate of the nonwoven fabric also affects the leukocyte removal performance. The filling rate of the nonwoven fabric used in the present invention is determined by measuring the area, thickness, and weight of the nonwoven fabric cut to arbitrary dimensions and the specific gravity of the material which makes up the nonwoven fabric, and calculating the filling rate using the following equation (1).

$$\text{Filling rate} = \{\text{weight of nonwoven fabric (g)}/(\text{area of nonwoven fabric (cm}^2) \times \text{thickness of nonwoven fabric (cm)})\}/\text{specific gravity of material making up nonwoven fabric (g/cm}^3) \qquad (1)$$

The filling rate is preferably 0.05 to 0.30, still more preferably 0.07 to 0.25, and particularly preferably 0.07 to 0.20. If the filling rate is greater than 0.30, the flow resistance of the nonwoven fabric is increased, whereby flowability is not preferable. On the other hand, if the filling rate is less than 0.05, leukocytes pass through the nonwoven fabric without being trapped by the nonwoven fabric, whereby the leukocyte removal performance is decreased. Moreover, the mechanical strength of the nonwoven fabric is unpreferably also decreased.

In microscopic observation of the nonwoven fabric, since the number of intersections of fibers is increased as the fiber dispersibility of the nonwoven fabric is improved, the leukocyte removal performance is improved due to an increase in the number of contact points (adsorption points) with leukocytes. Therefore, nonwoven fabric in which fibers are not unevenly distributed or bundled is preferable.

In microscopic observation of the nonwoven fabric, if the nonwoven fabric has a narrow pore size distribution and a certain average pore size, the leukocyte removal performance per unit volume is preferably improved.

Plural sheets of the nonwoven fabric used in the leukocyte removal method of the present invention are layered to form a leukocyte removal filter material. The leukocyte removal filter material is placed in a container having an inlet and an outlet for liquid to make up a leukocyte removal filter. The nonwoven fabric used in the leukocyte removal method of the present invention may make up the entire leukocyte removal filter material, or make up a part of the leukocyte removal filter material. For example, nonwoven fabric having a high formation index and/or a porous product having three-dimensional mesh-like continuous pores such as a sponge structure may be disposed on the upstream side, and nonwoven fabric having a low formation index may be disposed on the downstream side.

The shape of the leukocyte removal filter material is not particularly limited. For example, a material obtained by layering sheets of nonwoven fabric in the shape of a planar plate, and a material obtained by cylindrically forming the planar-plate-shaped material can be given. The former material has been widely used for a blood transfusion filter or the like, since it is compact and can be relatively easily formed. Since the latter material is suitable for the filtration of a large quantity of liquid, that material is preferably used as a filter for extracorporeal circulation.

The leukocyte removal filter material used in the present invention may be formed by a single filter material or by a plurality of filter materials. In the case where the leukocyte removal filter material may be formed by a plurality of filter materials, it is preferable that the leukocyte removal filter material comprises a first filter material disposed upstream for removing micro-aggregate, and a second filter material disposed downstream of the first filter material for removing leukocytes. For example, a filter material comprising nonwoven fabric having a fiber diameter of several to several tens of micrometers may be disposed on the inlet side as the first filter material for removing aggregate, a filter material comprising nonwoven fabric having a fiber diameter of 0.3 to 3.0 µm may be disposed as the second filter material for removing leukocytes, and, as required, a post-filter may be disposed downstream of the second filter material.

In the case of a leukocyte removal filter comprising a planar-shaped and flexible container, provision of the post-filter prevents the filter elements from being pressed against the container on the outlet side due to positive pressure on the inlet side produced during filtration, and prevents the container on the outlet side from adhering to the filter element and inhibiting the blood flow due to negative pressure on the outlet side. Moreover, weldability between the flexible container and the filter material is increased. As the post-filter, a conventional filter medium such as a fibrous porous medium such as nonwoven fabric, woven fabric, or mesh, or a porous product having three-dimensional mesh-like continuous pores may be used. As the material for the post-filter, polypropylene, polyethylene, styrene-isobutylene-styrene copolymer, polyurethane, polyester, and the like can be given. It is preferable that the post-filter be formed of nonwoven fabric from the viewpoint of productivity and weld strength of the leukocyte removal filter. It is particularly preferable that the post-filter have a plurality of protrusions formed by embossing or the like, since the blood flow becomes more uniform.

Each of the first and second filter materials may include different filter materials, or either the first or second filter materials may include different filter materials. For example, the first filter material comprising nonwoven fabric having a fiber diameter of 30 to 40 µm and/or nonwoven fabric having a fiber diameter of 10 to 20 µm may be disposed on the upstream side, and the second filter material comprising nonwoven fabric having a fiber diameter of 1.5 to 2.5 µm and/or nonwoven fabric having a fiber diameter of 0.5 to 1.8 µm may be disposed downstream of the first filter material. Nonwoven fabric with a large fiber diameter and nonwoven fabric with a small fiber diameter may be alternately disposed. It is preferable that the nonwoven fabric with a large fiber diameter be disposed on the upstream side.

In order to control the blood cell selective separation properties and surface hydrophilicity, the surface of the leukocyte removal filter material may be modified by using a known technology such as coating, chemical treatment, or radiation treatment.

As the material for the container in which the leukocyte removal filter material is placed, a hard resin or a flexible resin may be used. As to the hard resin, examples of the raw material thereof include a phenol resin, acrylic resin, epoxy resin, formaldehyde resin, urea resin, silicon resin, ABS resin, nylon, polyurethane, polycarbonate, polyvinyl chloride, polyethylene, polypropylene, polyester, styrene-butadiene copolymer, and the like. In the case of using the flexible resin, the container is preferably formed of a sheet-like or cylindrical formed product of a flexible synthetic resin. The material for the container preferably has thermal and electrical properties similar to those of the material for the filter element. For example, soft polyvinyl chloride, polyurethane, ethylene-vinyl acetate copolymer, polyolefin such as polyethylene and polypropylene, thermoplastic elastomer such as hydrogenated styrene-butadiene-styrene copolymer, styrene-isoprene-styrene copolymer, or hydrogenated styrene-isoprene-styrene copolymer, a mixture of the thermoplastic elastomer, and softener such as polyolefin, ethylene-ethyl acrylate, and the like can be given as suitable materials. Of these, soft polyvinyl chloride, polyurethane, ethylene-vinyl acetate copolymer, polyolefin, and thermoplastic elastomer containing these polymers as the major component are preferable, with soft polyvinyl chloride and polyolefin being particularly preferable.

The shape of the container is not particularly limited insofar as the container has an inlet for a leukocyte-containing liquid and an outlet for a leukocyte-free liquid. It is preferable that the container have a shape corresponding to the shape of the leukocyte removal filter material. In the case where the leukocyte removal filter material is in the shape of a planar plate, the shape of the container may be polygonal such as quadrilateral or hexagonal or a flat shape formed by a curve such as circular or elliptical. In more detail, it is preferable that the container include an inlet-side container having a liquid inlet and an outlet-side container having a liquid outlet, and the inlet-side container and the outlet-side container sandwich the leukocyte removal filter material directly or through a support to divide the inside of the filter in two rooms to form a flat leukocyte removal filter. As another example, in the case where the leukocyte removal filter material is cylindrical, it is preferable that the container also be cylindrical. In more detail, it is preferable that the container includes a cylindrical body in which the filter material, an inlet-side header including a liquid inlet, and an outlet-side header including a liquid outlet are accommodated. The inside of the container is divided in two by potting so that liquid introduced from the inlet flows from the outer circumferential side of the cylindrical filter to the inner circumferential side (or, from the inner circumferential section to the outer circumferential section) to form a cylindrical leukocyte removal filter.

The leukocyte removal method of the present invention is described below. An embodiment of a method for preparing each leukocyte-free blood product is described below. However, the present invention is not limited to the following embodiment.

(Preparation of Leukocyte-Free Whole Blood Product)

A preservative solution or anticoagulant such as CPD, CPDA-1, CP2D, ACD-A, ACD-B, or heparin is added to whole blood collected, and leukocytes are removed from the whole blood by using the leukocyte removal filter to obtain a leukocyte-free whole blood product.

In the case of removing leukocytes before storage, in the preparation of a leukocyte-free whole blood product, leukocytes are removed from whole blood which is stored at room temperature or under refrigeration preferably within 72 hours, still more preferably within 24 hours, particularly preferably within 12 hours, and most preferably within eight hours after collection using the leukocyte removal filter at room temperature or in cold storage to obtain a leukocyte-free whole blood product. In the case of removing leukocytes after storage, leukocytes are removed from whole blood stored at room temperature, under refrigeration, or under frozen preferably within 24 hours before use by using the leukocyte removal filter to obtain a leukocyte-free whole blood product.

(Preparation of Leukocyte-Free Red Cell Product)

A preservative solution or anticoagulant such as CPD, CPDA-1, CP2D, ACD-A, ACD-B, or heparin is added to whole blood collected. The separation method for each blood component is divided into a method for removing leukocytes from whole blood and centrifuging the resulting blood, and a method for centrifuging whole blood and removing leukocytes from red cells or red cells and BC.

In the case of centrifuging blood after removing leukocytes from whole blood, leukocyte-free whole blood is centrifuged to obtain a leukocyte-free red cell product.

In the case of centrifuging whole blood before removing leukocytes, the centrifugation conditions are divided into soft spin conditions where the whole blood is separated into red cells and PRP, and hard spin conditions where the whole blood is separated into red cells, BC, and PPP. After the addition of a preservative solution such as SAGM, AS-1, AS-3, AS-5, or MAP, as required, to red cells separated from whole blood or red cells containing BC, leukocytes are removed from red cells using the leukocyte removal filter to obtain a leukocyte-free red cell product.

In the preparation of the leukocyte-free red cell product, whole blood stored at room temperature or under refrigeration is centrifuged preferably within 72 hours, still more preferably within 48 hours, particularly preferably within 24 hours, and most preferably within 12 hours after collection. In the case of removing leukocytes before storage, leukocytes are removed from a red cell product stored at room temperature or under refrigeration preferably within 120 hours, still more preferably within 72 hours, particularly preferably within 24 hours, and most preferably within 12 hours after collection using the leukocyte removal filter at room temperature or under refrigeration to obtain a leukocyte-free red cell product. In the case of removing leukocytes after storage, leukocytes are removed from a red cell product stored at room temperature, under refrigeration, or under frozen preferably within 24 hours before use by using the leukocyte removal filter to obtain a leukocyte-free red cell product (Preparation of Leukocyte-Free Platelet Product)

A preservative solution or anticoagulant such as CPD, CPDA-1, CP2D, ACD-A, ACD-B, or heparin is added to whole blood collected.

As the separation method for each blood component, a method for removing leukocytes from whole blood and performing centrifugation, and a method for centrifuging whole blood and removing leukocytes from PRP or platelets can be given.

In the case of centrifuging blood after removing leukocytes from whole blood, a leukocyte-free platelet product is obtained by centrifuging the leukocyte-free whole blood.

In the case of centrifuging whole blood before removing leukocytes, the centrifugation conditions are divided into soft spin conditions where whole blood is separated into red cells and PRP, and hard spin conditions where whole blood is separated into red cells, BC, and PPP. Under the weak centrifugal conditions, leukocytes are removed from PRP separated from whole blood by using the leukocyte removal filter, and a leukocyte-free platelet product is obtained by centrifugation, or platelets and PPP are obtained by centrifuging PRP, and leukocytes are removed by using the leukocyte removal filter to obtain a leukocyte-free platelet product. Under the strong centrifugal conditions, one unit or several to about ten-odd units of BC separated from whole blood is centrifuged after adding a preservative solution, plasma, and the like, if desired, to obtain platelets, and leukocytes are removed from the resulting platelets by using the leukocyte removal filter to obtain a leukocyte-free platelet product.

In the preparation of the leukocyte-free platelet product, whole blood stored at room temperature is centrifuged preferably within 24 hours, still more preferably within 12 hours, and particularly preferably within eight hours after collection. In the case of removing leukocytes before storage, leukocytes are removed at room temperature from a platelet product which is stored at room temperature preferably within 120 hours, still more preferably within 72 hours, particularly preferably within 24 hours, and most preferably within 12 hours after collection by using the leukocyte removal filter to obtain a leukocyte-free platelet product. In the case of removing leukocytes after storage, leukocytes are removed from a platelet product stored at room temperature, under refrigeration, or under frozen preferably within 24 hours before use by using the leukocyte removal filter to obtain a leukocyte-free platelet product (Preparation of Leukocyte-Free Plasma Product)

A preservative solution or anticoagulant such as CPD, CPDA-1, CP2D, ACD-A, ACD-B, or heparin is added to whole blood collected.

As the separation method for each blood component, a method for removing leukocytes from whole blood and performing centrifugation thereafter, and a method for centrifuging whole blood and removing leukocytes from PPP or PRP can be given.

In the case of performing centrifugation after removing leukocytes from whole blood, a leukocyte-free plasma product is obtained by centrifuging leukocyte-free whole blood.

In the case of centrifuging whole blood before removing leukocytes, the centrifugation conditions are divided into soft spin conditions where whole blood is separated into red cells and PRP, and hard spin conditions where whole blood is separated into red cells, BC, and PPP. In the case of the soft spin conditions, leukocytes are removed from PRP by using the leukocyte removal filter, and a leukocyte-free plasma product is obtained by centrifugation, or PRP is separated into PPP and platelets by centrifugation, and leukocytes are removed by using the leukocyte removal filter to obtain a leukocyte-free plasma product In the case of the hard spin conditions, leukocytes are removed from PPP by using the leukocyte removal filter to obtain a leukocyte-free plasma product.

In the preparation of the leukocyte-free plasma product, whole blood stored at room temperature or under refrigeration is centrifuged preferably within 72 hours, still more preferably within 48 hours, particularly preferably within 24 hours, and most preferably within 12 hours after collection. Or, leukocytes are removed at room temperature or under refrigeration from a plasma product which is stored at room temperature or under refrigeration preferably within 120 hours, still more preferably within 72 hours, particularly preferably within 24 hours, and most preferably within 12 hours after collection by using the leukocyte removal filter to obtain a leukocyte-free plasma product. In the case of removing leukocytes after storage, leukocytes are removed from a plasma product stored at room temperature, under refrigeration, or under frozen preferably within 24 hours before use by using the leukocyte removal filter to obtain a leukocyte-free plasma product.

As the mode from blood collection to preparation of a leukocyte-free blood product, any mode such as a mode of collecting blood using a blood collection needle connected with a whole blood container, and connecting the container containing whole blood or blood components after centrifugation with the leukocyte removal filter to remove leukocytes, a mode of collecting blood using a circuit formed by sterilely connecting at least a blood collection needle, a blood container, and the leukocyte removal filter, and removing leukocytes before or after centrifugation, or a mode of connecting the leukocyte removal filter with a container containing blood components obtained using an automatic blood collection device or using the leukocyte removal filter connected in advance with the container to remove leukocytes may be used. However, the present invention is not limited to these modes. A leukocyte-free red cell product, a leukocyte-free platelet product, or a leukocyte-free plasma product may be obtained by centrifuging whole blood into each component using an automatic blood component collection device, optionally adding a preservative solution, and immediately causing any of red cells, BC-containing red cells, BC, platelets, PRP, or PPP to pass through the leukocyte removal filter to remove leukocytes.

The present invention exhibits a higher leukocyte removal performance for all types of blood mentioned above and has the effect of shortening the filtration time without causing clogging. The present invention is particularly suitable for a red cell filtration in which the blood filtration time tends to be elongated.

In the preparation of these blood products, leukocytes may be removed by allowing a leukocyte-containing blood to flow into the leukocyte removal filter from a container containing the leukocyte-containing liquid provided at a position higher than the leukocyte removal filter through a tube by utilizing head drop, or leukocytes may be removed by allowing the leukocyte-containing blood to flow by increasing pressure of the inlet side of the leukocyte removal filter and/or reducing pressure of the outlet side of the leukocyte removal filter using means such as a pump.

A leukocyte removal method using the leukocyte removal filter in extracorporeal circulation therapy is described below.

After priming the inside of the leukocyte removal filter using a physiological saline solution or the like, the liquid inside the leukocyte removal filter is replaced with a solution containing at least an anticoagulant such as heparin, nafamostat mesilate, ACD-A, ACD-B or the like. Blood is caused to flow into the inlet of the leukocyte removal filter from a circuit connected with a human at a flow rate 10 to 200 mL/min while adding the anticoagulant to the blood which is caused to flow from the body to remove leukocytes using the leukocyte removal filter. In the leukocyte removal start period (throughput: 0 to 0.5 L), the flow rate is preferably 10 to 50 mL/min, and still more preferably 20 to 40 mL/min. After the leukocyte removal start period (throughput: 0.2 to 12 L), the flow rate is preferably 30 to 120 mL/min, still more preferably 40 to 100 mL/min, and particularly preferably 40 to 60 mL/min. It is preferable to replace the liquid inside the leukocyte removal filter with a physiological saline solution or the like after removing leukocytes to return the blood, since the blood inside the leukocyte removal filter is not wasted.

EXAMPLES

The present invention is described below based on examples. However, the present invention is not limited to the following examples.

Example 1

Nonwoven fabric formed of polyethylene terephthalate (hereinafter abbreviated as "PET") and having a weight per square meter of 40 g/m$^2$, a thickness of 0.23 mm, a filling rate of 0.14, an average fiber diameter of 1.3 μm, and a formation index of 38.0 was used as a leukocyte removal filter material. The formation index was measured according to the above-described method.

A test method for evaluating the leukocyte removal performance is described below. Blood used for blood evaluation was whole blood prepared by adding 14 mL of a CPD solution as an anticoagulant to 100 mL of blood immediately after collection, stirring the resulting mixture, and allowing the mixture to stand for two hours (hereinafter called "pre-filtration blood"). A column with an effective filtration area of 1.3 cm$^2$ was packed with eight sheets of nonwoven fabric. A syringe filled with the pre-filtration blood was connected with the inlet of the column through a polyvinyl chloride tube having an inner diameter of 3 mm and an outer diameter of 4.2 mm. The blood was caused to flow through the column at a flow rate of 1.2 mL/min using a syringe pump to collect 3 mL of the blood (hereinafter called "post-filtration blood"). The leukocyte removal performance was evaluated by calculating the leukocyte residual rate. The leukocyte residual rate was determined by measuring the number of leukocytes using a flow cytometry method (apparatus: "FACS Calibur" manufactured by Becton, Dickinson and Company), and calculating the leukocyte residual rate according to the following equation (2).

Leukocyte residual rate=[leukocyte concentration (number/μL)(post-filtration blood)]/[leukocyte concentration (number/μL)(pre-filtration blood)] (2)

The number of leucocytes was measured by sampling 100 μl of each blood and using a leucocount kit with beads Nippon Becton Dickinson Co., Ltd.). A pressure gauge was connected with the tube connected with the inlet side of the column, and the pressure applied to the inlet side of the column at the completion of blood filtration was measured using the pressure gauge. The resulting value was defined as the blood filtration pressure.

Figure 1:
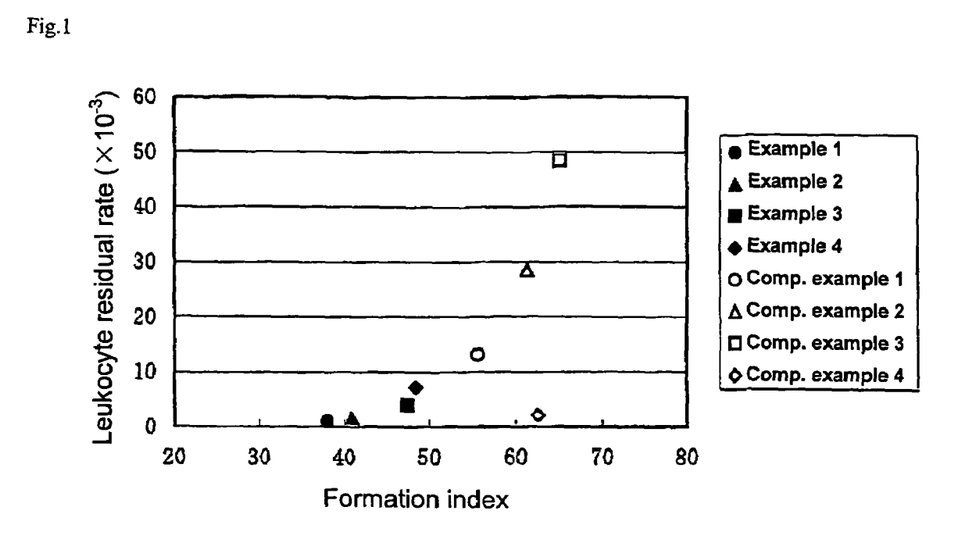
FIG. 1 is a graph showing the relationship between the formation index and the leukocyte residual rate of leukocyte removal filters of Examples 1 to 4 and Comparative Examples 1 to 4.
Figure 2:
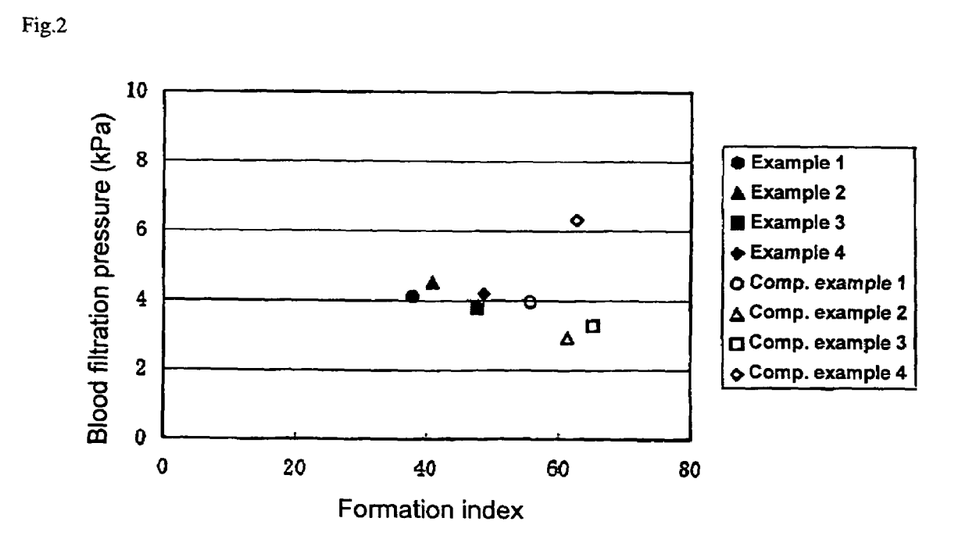
FIG. 2 is a graph showing the relationship between the formation index and the blood filtration pressure of the leukocyte removal filters of Examples 1 to 4 and Comparative Examples 1 to 4.

As a result, the leukocyte residual rate was $1.0 \times 10^{-3}$, and the blood filtration pressure was 4.7 kPa. The blood evaluation results of Examples 1 to 4 and Comparative Examples 1 to 4 are summarized in Table 1 and FIGS. 1 and 2.

Example 2

Nonwoven fabric formed of PET and having a weight per square meter of 40 g/m², a thickness of 0.23 mm, a filling rate of 0.14, an average fiber diameter of 1.3 μm, and a formation index of 40.9 was used as a leukocyte removal filter material. The blood test was conducted in the same manner as in Example 1. As a result, the leukocyte residual rate was $1.6 \times 10^{-3}$, and the blood filtration pressure was 4.5 kPa.

If the leukocyte residual rate becomes $10^{-4}$ or less, the number of residual leukocytes approximately reaches the measurement limit Therefore, in the above examples, the filter was prepared and tested under such conditions that the leukocyte residual rate became $10^{-4}$ or more. A filter ensuring a leukocyte residual rate of $10^{-4}$ to $10^{-6}$ necessary for preventing serious side effects can be obtained by designing a filter suitable for the amount of blood product subjected to the leukocyte removal filtration.

Example 3

Nonwoven fabric formed of PET and having a weight per square meter of 40 g/m², a thickness of 0.23 mm, a filling rate of 0.14, an average fiber diameter of 1.3 μm, and a formation index of 47.5 was used as a leukocyte removal filter material. The blood test was conducted in the same manner as in Example 1. As a result, the leukocyte residual rate was $4.0 \times 10^{-3}$, and the blood filtration pressure was 3.8 kPa.

Example 4

Nonwoven fabric formed of PET and having a weight per square meter of 40 g/m², a thickness of 0.22 mm, a filling rate of 0.14, an average fiber diameter of 1.6 μm, and a formation index of 48.5 was used as a leukocyte removal filter material. The blood test was conducted in the same manner as in Example 1. As a result, the leukocyte residual rate was $7.2 \times 10^{-3}$, and the blood filtration pressure was 4.2 kPa.

Comparative Example 1

Nonwoven fabric formed of PET and having a weight per square meter of 40 g/m², a thickness of 0.24 mm, a filling rate of 0.14, an average fiber diameter of 1.2 μm, and a formation index of 55.5 was used as a leukocyte removal filter material. The blood test was conducted in the same manner as in Example 1. As a result, the leukocyte residual rate was $13.2 \times 10^{-3}$, and the blood filtration pressure was 4.0 kPa.

Comparative Example 2

Nonwoven fabric formed of PET and having a weight per square meter of 39 g/m², a thickness of 0.24 mm, a filling rate of 0.13, an average fiber diameter of 1.3 μm, and a formation index of 61.3 was used as a leukocyte removal filter material. The blood test was conducted in the same manner as in Example 1. As a result, the leukocyte residual rate was $28.5 \times 10^{-3}$, and the blood filtration pressure was 2.9 kPa.

Comparative Example 3

Nonwoven fabric formed of PET and having a weight per square meter of 39 g/m², a thickness of 0.24 mm, a filling rate of 0.13, an average fiber diameter of 1.3 μm, and a formation index of 65.0 was used as a leukocyte removal filter material. The blood test was conducted in the same manner as in Example 1. As a result, the leukocyte residual rate was $48.4 \times 10^{-3}$, and the blood filtration pressure was 3.3 kPa.

Comparative Example 4

Nonwoven fabric formed of PET and having a weight per square meter of 40 g/m², a thickness of 0.23 mm, a filling rate of 0.13, an average fiber diameter of 0.9 μm, and a formation index of 62.6 was used as a leukocyte removal filter material. The blood test was conducted in the same manner as in Example 1. As a result, the leukocyte residual rate was $2.1 \times 10^{-3}$, and the blood filtration pressure was 6.3 kPa.

From the results of Examples 1 to 4 and Comparative Examples 1 to 4, it was found that a high leukocyte removal performance is obtained by reducing the formation index of the nonwoven fabric without causing a significant increase in the blood filtration pressure. These results also suggest that, although the leukocyte removal performance is increased by reducing the fiber diameter of the nonwoven fabric having a high formation index, such nonwoven fabric is not suitable for the leukocyte removal filter since the blood filtration pressure is increased to a large extent.

Example 5

(1) An inlet-side flexible container having a blood inlet and formed of a polyvinyl chloride resin sheet, (2) four sheets of PET nonwoven fabric having a weight per square meter of 30 g/m², a thickness of 0.19 mm, and an average fiber diameter of 12 μm, (3) 25 sheets of PET nonwoven fabric having a weight per square meter of 40 g/m², a thickness of 0.23 mm, a filling rate of 0.14, an average fiber diameter of 1.3 μm, and a formation index of 38.0, (4) four sheets of PET nonwoven fabric having a weight per square meter of 30 g/m², a thickness of 0.19 mm, and an average fiber diameter of 12 μm, and (5) an outlet-side flexible container having a blood outlet and formed of a polyvinyl chloride resin sheet were disposed in that order. The filter materials (2) to (4) were welded while sandwiched between the inlet-side flexible container (1) and the outlet-side flexible container (5) so that the vicinities of the peripheral sections were integrated with the flexible containers over the entire circumference to prepare a filter with dimensions of the filtration section of 7.5 cm×5.8 cm.

A flowability test method for the blood treatment filter is described below. The blood treatment filter of the present invention was disposed between a reservoir bag and a recovery bag. An inlet-side tube connected with the reservoir bag was connected with the blood inlet of the blood treatment filter, and an outlet-side tube connected with the recovery bag was connected with the blood outlet of the blood treatment filter. A polyvinyl chloride tube having an inner diameter of 3 mm, an outer diameter of 4.2 mm, and a length of 50 cm was used as each tube. After closing the inlet-side tube using a clamp, 300 g of bovine blood was placed in the reservoir bag. As the bovine blood, bovine red cell concentrate prepared by using the following method was used.

After collecting blood from a bovine, CPD is added to the blood as an anticoagulant at a ratio of 123 mL CPD/1 L bovine blood, and the mixture is stored overnight at 20° C. After removing foreign matters and aggregate using gauze or the like, the whole blood is separated into red cells, BC, and plasma by centrifugation. After removing only the plasma from the whole blood centrifuged, SAGM is added as a red cell preservative solution so that the hematocrit value becomes 60% to prepare bovine red cell concentrate.

After suspending the entire system and placing the recovery bag on a balance, the clamp closing the inlet-side tube was released to start filtration. The period of time until the reservoir bag containing the bovine red cell concentrate becomes empty after the bovine red cell concentrate reached the recovery bag was defined as the filtration time. After the reservoir bag became empty, the value indicated by the balance on which the recovery bag was placed was read every minute. The recovery was terminated when a change in the value of the balance within one minute became 0.1 g or less, and the value indicated by the balance when terminating the recovery was defined as the amount recovered. The blood recovery rate was calculated using the following equation.

Blood recovery rate (%)=100 (%)×amount recovered (g)/300 (g)

Figure 3:
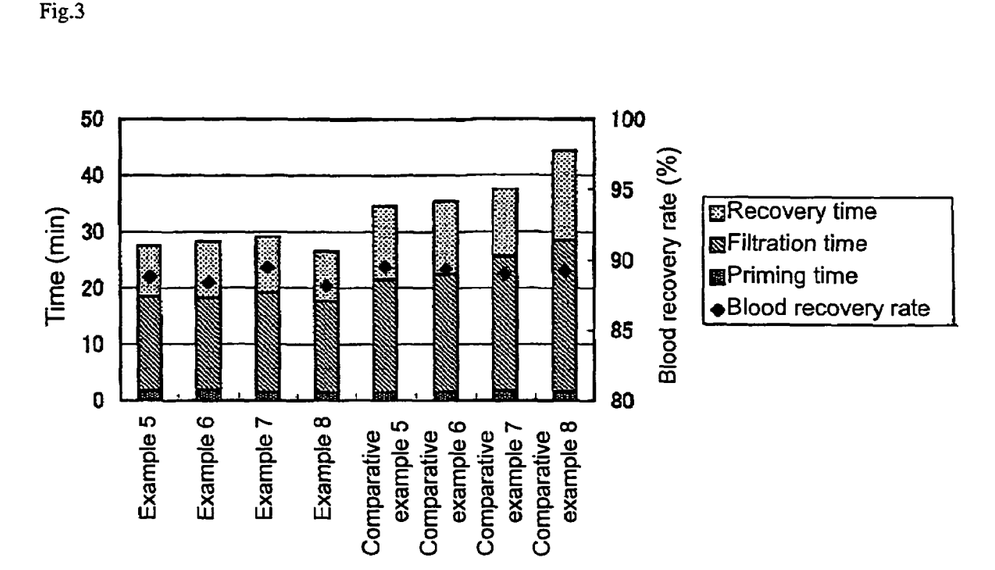
FIG. 3 is a graph showing the blood recovery rate and the time required for a series of operations for leukocyte removal filters of Examples 5 to 8 and Comparative Examples 5 to 8.

The blood evaluation results of Examples 5 to 8 and Comparative Examples 5 to 8 are summarized and shown in Table 2 and FIG. 3.

Example 6

The priming time, filtration time, recovery time, and blood recovery rate were determined by using the same filter configuration and evaluation method as those of Example 5 except for using 25 sheets of PET nonwoven fabric having a weight per square meter of 40 g/m², a thickness of 0.23 mm, a filling rate of 0.14, an average fiber diameter of 1.3 µm, and a formation index of 40.9 as (3).

Example 7

The priming time, filtration time, recovery time, and blood recovery rate were determined by using the same filter configuration and evaluation method as those of Example 5 except for using 25 sheets of PET nonwoven fabric having a weight per square meter of 40 g/m², a thickness of 0.23 mm, a filling rate of 0.14, an average fiber diameter of 1.3 µm, and a formation index of 47.5 as (3).

Example 8

The priming time, filtration time, recovery time, and blood recovery rate were determined by using the same filter configuration and evaluation method as those of Example 5 except for using 25 sheets of PET nonwoven fabric having a weight per square meter of 40 g/m², a thickness of 0.22 mm, a filling rate of 0.14, an average fiber diameter of 1.6 µm, and a formation index of 48.5 as (3).

Comparative Example 5

The priming time, filtration time, recovery time, and blood recovery rate were determined by using the same filter configuration and evaluation method as those of Example 5 except for using 25 sheets of PET nonwoven fabric having a weight per square meter of 40 g/m², a thickness of 0.24 mm, a filling rate of 0.14, an average fiber diameter of 1.2 µm, and a formation index of 55.5 as (3).

Comparative Example 6

The priming time, filtration time, recovery time, and blood recovery rate were determined by using the same filter configuration and evaluation method as those of Example 5 except for using 25 sheets of PET nonwoven fabric having a weight per square meter of 39 g/m², a thickness of 0.24 mm, a filling rate of 0.13, an average fiber diameter of 1.3 µm, and a formation index of 61.3 as (3).

Comparative Example 7

The priming time, filtration time, recovery time, and blood recovery rate were determined by using the same filter configuration and evaluation method as those of Example 5 except for using 25 sheets of PET nonwoven fabric having a weight per square meter of 39 g/m², a thickness of 0.24 mm, a filling rate of 0.13, an average fiber diameter of 1.3 µm, and a formation index of 65.0 as (3).

Comparative Example 8

The priming time, filtration time, recovery time, and blood recovery rate were determined by using the same filter configuration and evaluation method as those of Example 5 except for using 25 sheets of PET nonwoven fabric having a weight per square meter of 40 g/m², a thickness of 0.23 mm, a filling rate of 0.13, an average fiber diameter of 0.9 µm, and a formation index of 62.6 as (3).

From the results of Examples 5 to 8 and Comparative Examples 5 to 8, it was found that the leukocyte removal filter comprising the nonwoven fabric with a low formation index reduces the filtration time while maintaining an equal blood recovery rate. The filtration time was elongated when using the leukocyte removal filter cpmprising the nonwoven fabric with a high formation index and a small fiber diameter.

TABLE 1

|  | Example | | | | Comparative Example | | | |
| --- | --- | --- | --- | --- | --- | --- | --- | --- |
|  | 1 | 2 | 3 | 4 | 1 | 2 | 3 | 4 |
| Weight per square meter (g/m²) | 40 | 40 | 40 | 40 | 40 | 39 | 39 | 40 |
| Thickness (mm) | 0.23 | 0.23 | 0.23 | 0.22 | 0.24 | 0.24 | 0.24 | 0.23 |
| Filling rate | 0.14 | 0.14 | 0.14 | 0.14 | 0.14 | 0.13 | 0.13 | 0.13 |
| Average fiber diameter (µm) | 1.3 | 1.3 | 1.3 | 1.6 | 1.2 | 1.3 | 1.3 | 0.9 |

TABLE 1-continued

|  | Example | | | | Comparative Example | | | |
|---|---|---|---|---|---|---|---|---|
|  | 1 | 2 | 3 | 4 | 1 | 2 | 3 | 4 |
| Formation index | 38.0 | 40.9 | 47.5 | 48.5 | 55.5 | 61.3 | 65.0 | 62.6 |
| Leukocyte residual rate ($\times 10^{-3}$) | 1.0 | 1.6 | 4.0 | 7.2 | 13.2 | 28.5 | 48.4 | 2.1 |
| Filtration pressure (kPa) | 4.1 | 4.5 | 3.8 | 4.2 | 4.0 | 2.9 | 3.3 | 6.3 |

TABLE 2

|  | Example | | | | Comparative Example | | | |
|---|---|---|---|---|---|---|---|---|
|  | 5 | 6 | 7 | 8 | 5 | 6 | 7 | 8 |
| Weight per square meter (g/m$^2$) | 40 | 40 | 40 | 40 | 40 | 39 | 39 | 40 |
| Thickness (mm) | 0.23 | 0.23 | 0.23 | 0.22 | 0.24 | 0.24 | 0.24 | 0.23 |
| Filling rate | 0.14 | 0.14 | 0.14 | 0.14 | 0.14 | 0.13 | 0.13 | 0.13 |
| Average fiber diameter (μm) | 1.3 | 1.3 | 1.3 | 1.6 | 1.2 | 1.3 | 1.3 | 0.9 |
| Formation index | 38.0 | 40.9 | 47.5 | 48.5 | 55.5 | 61.3 | 65.0 | 62.6 |
| Priming time (min) | 1.7 | 1.8 | 1.5 | 1.5 | 1.4 | 1.4 | 1.7 | 1.5 |
| Filtration time (min) | 16.8 | 16.5 | 17.7 | 16.1 | 20.1 | 21.0 | 23.9 | 27.0 |
| Recovery time (min) | 9 | 10 | 10 | 9 | 13 | 13 | 12 | 16 |
| Blood recovery rate (%) | 88.8 | 88.5 | 89.5 | 88.2 | 89.6 | 89.3 | 89.0 | 89.2 |

INDUSTRIAL APPLICABILITY

According to the leukocyte removal method of the present invention, the leukocyte removal performance can be increased in comparison with a conventional method and the filtration time can be reduced without occurrence of clogging by using the leukocyte removal filter in which a specific structure in the thickness direction, that is, the liquid flow direction, is made uniform over the entire filtration surface. It is extremely effective to use the leukocyte removal method and the leukocyte removal filter of the present invention for trapping leukocytes mixed in blood.

The invention claimed is:

1. A leukocyte removal filter for removing leukocytes from a leukocyte-containing liquid, comprising: nonwoven fabric having an average fiber diameter of 0.3 to 3.0 μm, and a formation index y of 50 or less calculated for a nonwoven fabric having a thickness of 0.3 mm.

2. The leukocyte removal filter according to claim 1, wherein the nonwoven fabric has a filling rate of 0.05 to 0.30.

3. The leukocyte removal filter according to claim 1, wherein y satisfies the following inequality:

$y < -4 \times$ average fiber diameter of nonwoven fabric (μm)$+55$.

4. The leukocyte removal filter according to claim 1, wherein the nonwoven fabric comprises melt-blown fibers.

5. The leukocyte removal filter according to claim 1, comprising at least one of a filter for removing aggregate upstream of the nonwoven fabric and a post-filter downstream of the nonwoven fabric.

6. The leukocyte removal filter according to claim 1, comprising a flat filter having an inlet and an outlet for liquid.

7. The leukocyte removal filter according to claim 1, comprising a cylindrical filter having an inlet and an outlet for liquid.

8. The leukocyte removal filter according to claim 6, wherein a container of the flat filter is formed of a flexible resin.

9. The leukocyte removal filter according to claim 1, wherein the leukocyte removal filter removes leukocytes from a leukocyte-containing liquid comprising whole blood, red cell concentrate, platelet concentrate, platelet rich plasma, or platelet poor plasma.

10. The leukocyte removal filter of claim 1, wherein the nonwoven fabric comprises melt-blown fibers, and has a filling rate of 0.05 to 0.30 and satisfies the following inequality:

$y < -4 \times$ average fiber diameter of nonwoven fabric (μm)$+55$.

* * * * *